United States Patent [19]

Zofchak et al.

[11] Patent Number: 5,707,612
[45] Date of Patent: Jan. 13, 1998

[54] USE URETHANE POLYMERS OF CASTOR OIL SKIN AND PERSONAL CARE PRODUCT COMPOSITIIONS

[75] Inventors: Albert Zofchak, Matawan; John Obeji, Clifton; Michael Mosquera, Forked River, all of N.J.

[73] Assignee: Alzo, Inc., Matawan, N.J.

[21] Appl. No.: 629,005

[22] Filed: Apr. 8, 1996

[51] Int. Cl.$^6$ .................................................. A61K 7/035
[52] U.S. Cl. .......................... 424/69; 424/61; 424/64; 424/70.1; 424/70.11; 424/70.16; 424/78.02; 424/78.03; 512/8; 512/22; 514/844; 514/847; 514/845; 514/846
[58] Field of Search .................................. 424/61, 64, 69, 424/70.1, 70.11, 70.16, 78.02, 78.03; 512/8, 22; 514/844, 847, 845, 846

[56] References Cited

U.S. PATENT DOCUMENTS

| | | | |
|---|---|---|---|
| 2,266,777 | 12/1941 | Lieser | 424/330 |
| 2,282,827 | 5/1942 | Rothrock | 424/78 |
| 2,284,637 | 6/1942 | Catlin | 424/60 |
| 2,284,896 | 6/1942 | Hanford et al. | 424/54 |
| 2,511,544 | 6/1950 | Rinke et al. | 424/180 |
| 2,729,618 | 1/1956 | Muller et al. | 424/260 |
| 2,814,605 | 11/1957 | Stillmar | 424/240 |
| 2,858,298 | 10/1958 | Burt | 424/241 |
| 2,871,226 | 1/1959 | McShane | 424/330 |
| 2,915,496 | 12/1959 | Swart et al. | 424/78 |
| 2,948,691 | 8/1960 | Windemuth et al. | 424/60 |
| 3,049,514 | 8/1962 | Damusis | 424/54 |
| 3,049,515 | 8/1962 | Damusis | 424/180 |
| 3,049,516 | 8/1962 | Damusis | 424/241 |
| 3,472,931 | 10/1969 | Stoughton | 424/330 |
| 3,477,977 | 11/1969 | Schnell et al. | 424/78 |
| 3,539,482 | 11/1970 | Stewart | 528/60 |
| 3,551,554 | 12/1970 | Herschler | 424/54 |
| 3,594,409 | 7/1971 | Lachampt et al. | 424/180 |
| 3,797,494 | 3/1974 | Zaffaroni | 128/260 |
| 3,822,238 | 7/1974 | Blair et al. | 424/240 |
| 3,867,528 | 2/1975 | Ritter et al. | 424/241 |
| 3,968,245 | 7/1976 | Higuchi | 424/330 |
| 3,975,350 | 8/1976 | Hudgin et al. | 424/78 |
| 3,989,816 | 11/1976 | Rajadhyaksha | 424/60 |
| 4,006,218 | 2/1977 | Sipos | 424/54 |
| 4,039,664 | 8/1977 | Stoughton et al. | 424/180 |
| 4,060,084 | 11/1977 | Chandrasekaran et al. | 128/260 |
| 4,079,028 | 3/1978 | Emmons et al. | 424/54 |
| 4,130,667 | 12/1978 | Smith et al. | 424/361 |
| 4,155,892 | 5/1979 | Emmons et al. | 424/358 |
| 4,245,110 | 1/1981 | Engelhard et al. | 560/160 |
| 4,246,261 | 1/1981 | Van Scott et al. | 424/240 |
| 4,287,214 | 9/1981 | Van Scott et al. | 424/346 |
| 4,316,893 | 2/1982 | Rajadhyaksha | 424/180 |
| 4,405,616 | 9/1983 | Rajadhyaksha | 424/244 |
| 4,424,234 | 1/1984 | Alderson et al. | 424/317 |
| 4,440,777 | 4/1984 | Zupan | 424/274 |
| 4,483,759 | 11/1984 | Szycher et al. | 204/159.24 |
| 4,523,005 | 6/1985 | Szycher et al. | 528/76 |
| 4,543,405 | 9/1985 | Ambrose et al. | 528/78 |
| 4,568,343 | 2/1986 | Looper et al. | 604/896 |
| 4,614,787 | 9/1986 | Szycher et al. | 528/75 |
| 4,638,043 | 1/1987 | Szycher et al. | 528/78 |
| 4,704,303 | 11/1987 | Cornell | 427/53.1 |
| 4,710,497 | 12/1987 | Heller et al. | 514/221 |
| 4,731,241 | 3/1988 | Yamada et al. | 514/227 |
| 4,732,892 | 3/1988 | Sarpotdar et al. | 514/178 |
| 4,746,675 | 5/1988 | Makino et al. | 514/423 |
| 4,797,273 | 1/1989 | Linn et al. | 424/59 |
| 4,839,161 | 6/1989 | Bowser et al. | 424/59 |
| 4,847,072 | 7/1989 | Bissett et al. | 424/59 |
| 4,863,738 | 9/1989 | Taskovich | 424/449 |
| 4,885,174 | 12/1989 | Bodor et al. | 424/450 |
| 4,971,800 | 11/1990 | Chess et al. | 424/449 |
| 5,000,945 | 3/1991 | Kobayashi et al. | 424/59 |
| 5,008,100 | 4/1991 | Zecchino et al. | 424/59 |
| 5,017,365 | 5/1991 | Niedbala | 424/59 |
| 5,028,011 | 7/1991 | Schiffers | 242/56 |
| 5,032,390 | 7/1991 | Iwaya et al. | 424/59 |
| 5,045,317 | 9/1991 | Chess et al. | 424/401 |
| 5,051,260 | 9/1991 | Chess et al. | 424/449 |
| 5,089,250 | 2/1992 | Forestier et al. | 424/43 |
| 5,116,604 | 5/1992 | Fogel et al. | 424/59 |
| 5,207,998 | 5/1993 | Robinson et al. | 424/449 |
| 5,219,558 | 6/1993 | Woodin, Jr. et al. | 424/59 |
| 5,300,694 | 4/1994 | Smith et al. | 568/608 |
| 5,302,376 | 4/1994 | Forestier et al. | 424/59 |
| 5,338,539 | 8/1994 | Raspanti | 424/59 |

FOREIGN PATENT DOCUMENTS

| | | |
|---|---|---|
| 2557576 | 7/1985 | France . |
| 2948670 | 7/1980 | Germany . |
| 1179231 | 1/1970 | United Kingdom . |

OTHER PUBLICATIONS

Franz, J. Invest. Dermatol. 64:190–195 (1975).
"The Finite Dose Technique as a Valid In Vitro Model for the Study of Percutaneous Absorbtion in Man", in Current Problems in Dermatology, vol. 7, pp. 58–68, Ed. J.W.H. Mali (Karger, Basel, 1978).
Kambic et al., C& EN, "Biomaterials in Artificial Organs", Apr. 14, 1986, pp. 31–48.

Primary Examiner—Terressa Mosley
Attorney, Agent, or Firm—Coleman & Sudol

[57] ABSTRACT

This disclosure introduces the use of an isophorone diisocyanate urethane polymer of naturally occurring castor oil as an active ingredient for skin and personal care compositions and products.

10 Claims, No Drawings

USE URETHANE POLYMERS OF CASTOR OIL SKIN AND PERSONAL CARE PRODUCT COMPOSITIIONS

BACKGROUND OF THE INVENTION

1. Field of the Invention

Castor Oil and Castor Oil derivatives have been used for many years in cosmetic formulations. Esters of Castor Oil have been used as emollients in creams and lotions. Ethoxylated Castor Oils have been used as emulsifiers and solubilizing agents in the textile and cosmetic industries for decades. Ethoxylated/Hydrogenated Castor Oils have also functioned as waxes, emulsifiers and solubilizers and have been in use for the past thirty years in the coating industry where long lasting sheen and durability were of paramount concern. Urethanes based on methylene bisdiisocyanate have been used in the potting industry based on Castor Oil as well.

In the cosmetic industry, Castor Oil derivatives have appeared as amides to increase viscosity and enhance "conditioning" to hair formulations. Castor Oil amides have also functioned as emulsifiers. Sulfosuccinates based on derivatives of Castor Oil have been used for their mildness, foaming ability and anti-dandruff properties in addition to thickening. Betaines as well as amine oxides derived from the dimethylamidopropyl amine derivatives of castor oil have found use in the hair industry as viscosity improvers as well as conditioners, specifically when used on the acid side.

Castor Oil itself has been used as a vehicle in lipstick formulations where its low cost and description as a vegetable derived raw material, its low inherent toxicity and dispersing ability for pigments make it to be an ideal ingredient. Castor Oil is also used in lip glosses widely because of its characteristic property of sheen.

In spite of the wide use of Castor Oil in lipsticks and lip glosses there is a need for raw material in cosmetic formulations, hopefully, to increase adhesion, durability, gloss, increase product stability and exhibit a low order of toxicity. The present invention fulfills the long standing need for a safe, effective cosmetic ingredient demonstrating zero comedogenicity, lack of eye irritation low skin irritation and extremely low LD 50. To date, no existing polymers when evaluated against the subject invention exhibited similar overall familiar properties.

2. Prior Art a) U.S. Pat. No. 4,797,273 introduces water-in-oil microemulsions suitable for cosmetic use containing moisturizing agents or sunscreens.

b) U.S. Pat. No. 4,839,161 teaches a therapeutic composition for alleviating or preventing sun-induced desquamation.

c) U.S. Pat. No. 4,847,072 presents pharmaceutical compositions containing tocopherol sorbate which are useful in preventing damage to the skin caused by chronic or acute UV exposure.

d) U.S. Pat. No. 4,971,800 shows methods and compositions for enhancing the cutaneous penetration of topically or transdermally delivered pharmacologically active agents.

e) U.S. Pat. No. 5,000,945 preaches UV and UVB absorbing compounds.

f) U.S. Pat. No. 5,008,100 describes oil-in-water emulsions containing polyethylene as sunscreen compositions.

g) U.S. Pat. No. 5,017,365 shows sunscreen compositions and an application system.

h) U.S. Pat. No. 5,032,390 use ZnO in an anti-suntan cosmetic composition.

i) U.S. Pat. No. 5,045,317 deals with methods and compositions for enhancing the cutaneous penetration of topically or transdermally delivered pharmacologically active agents.

j) U.S. Pat. No. 5,051,260 is a C.I.P. of U.S. Pat. No. 4,971,800 again stressing cutaneous penetration of topically or transdermally delivered pharmacologically active agents.

k) U.S. Pat. No. 5,089,250 is titled "Cosmetic Containing Benzotiazole Diorganopolysiloxanes".

l) U.S. Pat. No. 5,116,604 teaches sunscreen compositions containing novel neopentanoate esters.

m) U.S. Pat. No. 5,207,998 discloses sun care compositions.

n) U.S. Pat. No. 5,028,011 indicates various ultraviolet resistant sunscreen formulations.

o) U.S. Pat. No. 5,219,558 provides photoprotection compositions having improved substantively to prevent sunburn and sun-induced premature skin aging.

p) U.S. Pat. No. 5,300,694 introduces alkoxylated compounds then use in cosmetic stick formulation.

q) U.S. Pat. No. 5,302,376 relates to a cosmetic emulsion screening out UV radiation.

r) U.S. Pat. No. 5,338,539 presents benzofuran derivatives.

OBJECTS AND SUMMARY OF THE INVENTION

Castor Oil has long been used in skin and hair formulations. Its use in these formulations suffers from odor and color problems, the bane of skin and hair formulations.

The use of the isophorone diisocyante urethane polymer derived from naturally occurring castor oil introduces a novel compound for these formulations to enhance adhesion, durability, emolliency, as well as gloss to skin and hair products.

This polymer offers new unanticipated synergistic results over and above the use of castor oil, castor oil esters, castor oil ethoxylates and propoylates and linear polyoxypropylene glycol urethanes.

The polymer herein introduced for this use exhibits decreased odor and diminished color making it cosmetically more desirable material than pure castor oil. It exhibits outstanding adhesion to skin and hair, exhibits long lasting emolliencey, enhances gloss for longer periods of time than Castor Oil Esters and other Castor Oil derivatives, assists in enhancing color dispersion, aids in durability, increases payoff in lipsticks and creams, helps to form an impenetrable water film, prevents feathering in lipsticks and helps eliminate bleeding in lipsticks. The urethane polymer of castor oil based on this method of synthesis forms a unique additive for cosmetics which is completely non-comodegeic, nonirritating to the skin and eyes and enhances the life and efficiency of a given cosmetic formulation.

This unique castor oil derivative in lipstick formulations gives the following results:

1. Immensely better dispersion of pigments (as opposed to straight castor oil). This results in an enhancement of color using less pigment therefore reducing raw materials of formulations.

2. Better fill in of the lips using this product as opposed to Castor oil.

3. Increased sheen and gloss as opposed to Castor oil.

4. Better application (glide) with the use of the present polyurethane castor oil formulated lipstick.

5. Increased adhesion and longer lasting lipsticks when based on the present urethane castor oil polymer as opposed to castor oil alone.

6. Increased moisturization of lipsticks when the urethane castor oil polymer is incorporated into lipsticks rather than straight castor oil.

DETAILED DESCRIPTION OF THE INVENTION

The present invention introduces the use of the reaction product of isophorone disocyanate and purified castor oil in the preparation of cosmetic formulations for the purpose of increased adhesion and tenacity as well as durability to the skin and hair. The inclusion of the present invention in a formulation provides a finished product which is resistant to removal from the skin and hair by repeated washing. Additionally higher gloss in lipsticks and lip glosses have been found when compared to use of castor oil itself as well as other linear polymers.

The preferred embodiment of the invention is as follows:

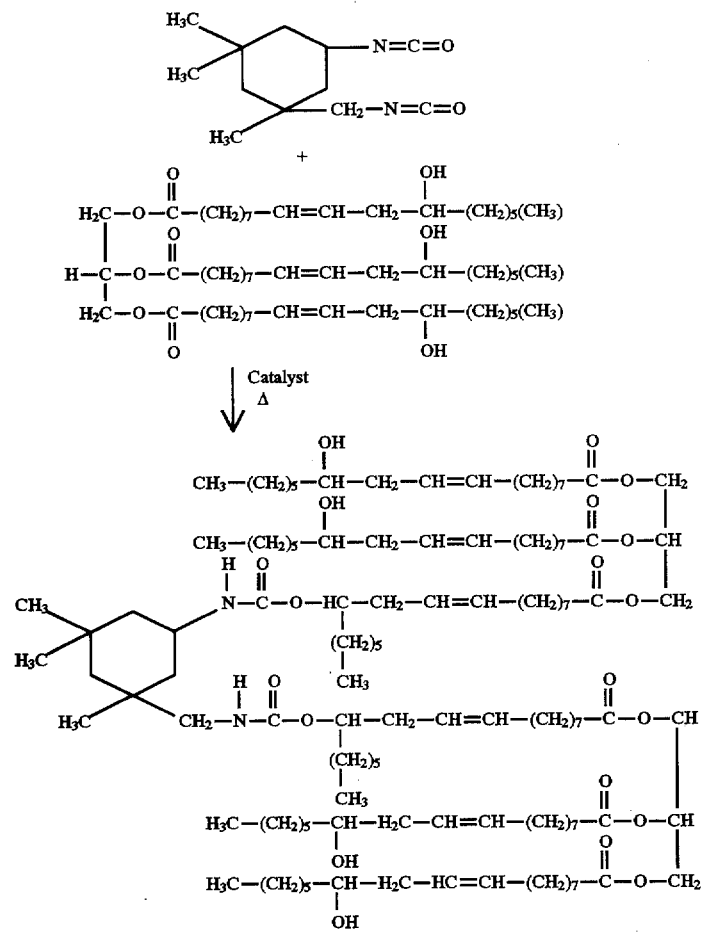

Naturally occurring Castor Oil has the following composition:

|  | % |
|---|---|
| Oleic | 7.4 |
| Linoleic | 3.1 |
| Linolenic | 1.9 |
| Ricinoleic | 87.0 |
| Dihydroxystearic | 0.6 |
|  | 100.0 |

The stoichiometric use of two moles of Castor Oil to one mole of isophorone diisocyanate gives the resulting preferred embodiment of the invention as shown above.

Attached hereto is a technical bulletin giving the physical and chemical data of the instant invention.

Acute oral toxicity test results in rats, under the Federal Hazardous Substances Act according to definitions listed in 16 CFR 1500.3 (c)(2)(i) indicate no toxicity.

Eye irritation tested pursuant to the Federal Hazardous Substances Act, 16 CFR, Section 1500.42 indicate that the material is not considered as primary eye irritant.

Tests of the material pursuant to the Federal Hazardous Substances Act, 16 CFR, Section 1500.3 (c)(4) show that the material introduced is not a primary skin irritant and is non-comedogenic.

Following are sample formulations using the instant invention:

TECHNICAL BULLETIN

POLYDERM PPI-CO

| | |
|---|---|
| Chemical Name | Castor Oil Polymer with 3-Isocyanatomethyl-3,5,5-Trimethylcyclohexyl Isocyanate |
| INCI Name | Castor Oil/IPDI Copolymer |
| CA Index Name | Castor Oil, Polymer with 5-Isocyanato-1-(Isocyanatomethyl)-1,3,3-Trimethylcyclohexane |
| CAS Number | 68955-90-8 |

SPECIFICATIONS:

| | |
|---|---|
| Appearance @ 25° C. | Clear Viscous Liquid |
| Color | Yellow |
| Odor | Mild Organoleptic |
| Specific Gravity (Typical) | 0.980 |
| Pounds per Gallon | 8.16 |
| Refractive Index @ 25° C. | 1.4825 |
| Molecular Weight (Approx.) | 2082 |
| Viscosity, cps @ 25° C. | 7,000 |
| Flash Point, °C. (C.O.C.) | Over 170° C. |
| SOLUBILITY: | Soluble in most organic solvents such as alcohols, ketones, glycol ethers and esters. Partially soluble in vegetable oil. Dispersible in mineral oil. Insoluble in silicones, glycols, diols, triols and water. |

SUGGESTED APPLICATIONS:

POLYDERM PPI-CO is a polymeric emollient where the triol is a derivative of castor oil. It offers outstanding adhesion characteristics for both hair and skin. Also, it provides effective water repellency and durability and forms a water resistant film even after repeated washings. This adhesive tenacity suggests use in sunscreens, lipsticks, protective creams and lotions for dry skin.

This information is believed to be reliable, but it is not to be construed as a warranty and no patent liability can be assumed.

BULLETIN #1202-1
MAY 1995

FORMULARY
POLYMERIC PROTECTIVE MOISTURIZING CREAM

| | INGREDIENTS | %, WEIGHT | INCI NAME |
|---|---|---|---|
| A. | Wickenol 707[1] | 4.00 | PPG-30 Cetyl Ether |
| | Dermol DIPS[1] | 3.00 | Diisopropyl Sebacate |
| | Dermol MOS[1] | 5.00 | Isostearyl Neopentanoate Isocetyl Stearate |
| | Polyderm PPI-CO[1] | 3.00 | N/A |
| | Stearic Acid-TP | 4.00 | Stearic Acid |
| | Dermol PGMS[1] | 6.00 | Propylene Glycol Stearate |
| | Cetyl Alcohol | 1.00 | Cetyl Alcohol |
| B. | Water, Deionized | 67.80 | |
| | Dowicil-200[2] | 0.20 | Quaternium-15 |
| | Triethanolamine | 1.00 | Triethanolamine |
| | Foamid AME-70 | 5.00 | Acetamide MEA |
| C. | Fragrance | q.s. | |

PROCEDURE:

1. Heat Part A 70–75° C.
2. Heat Part B 70–75° C.
3. With slow agitation, add Part B to Part A.
4. With constant agitation, allow batch to cool to 40° C.
5. Add fragrance.

[1]ALZO INC.
[2]DOW CHEMICAL
AUGUST 1995

FORMULARY
LIP CREAM

| | INGREDIENTS | %, WEIGHT |
|---|---|---|
| A. | DERMOL GMS-SE[1] | 12.00 |
| | DERMOL 135[1] | 10.00 |
| | Mineral Oil | 15.00 |
| | Promulgen D | 2.00 |
| | POLYDERM PPI-CO[1] | 1.00 |
| | Cetyl Alcohol | 3.00 |
| B. | Water (Deionized) | 48.00 |
| | FOAMQUAT SAQ-90[1] | 3.00 |
| | Propylene Glycol | 5.00 |
| C. | Germaben II (Propylene Glycol (and) Diazolidinyl Urea (and) Methylparaben (and) Propylparaben) | 1.00 |

PROCEDURE:

In a suitable vesel, weigh Phase A and heat to 80° C. In another vessel able to contain the entire batch, weigh Phase B and heat to 80° C. Slowly add Phase A to Phase B with agitation and mix for 10 minutes. Maintaining agitation, start cooling to 45° C. and add Phase C. Continue cooling and agitation to 25–28° C. and package.

[1]ALZO INC.

FORMULARY
DRY SKIN CREAM

| | INGREDIENTS | %, WEIGHT |
|---|---|---|
| A. | Triple Pressed Stearic Acid | 4.00 |
| | DERMOL 135[1] | 6.00 |
| | DERMOL 20-SD[1] | 2.00 |
| | Lanolin Oil | 0.50 |
| | Myrj 52S (PEG-40 Stearate | 2.00 |
| | Mineral Oil | 5.00 |
| | Abil B 8852 (Dimethiconecopolyol) | 1.00 |
| | POLYDERM PPI-CO | 1.00 |
| | DERMOL GMS-SE | 3.00 |
| | Vitamin E Acetate (Tocopheryl Acetate) | 0.10 |
| B. | Water (Deionized) | 55.00 |
| | Propylene Glycol | 3.00 |
| | Allantoin | 0.20 |
| | Triethanolamine, 99% | 0.90 |
| C. | Carbopol 934 2% Aq. Soln. (Carbomer 934) | 15.00 |
| D. | Germaben IIE (Propylene Glycol (and) Diazolidinyl Urea (and) Methylparaben (and) Propylparaben) | 1.00 |
| E. | Fragrance | 0.30 |
| | | 100.00% |

[1]ALZO INC.

FORMULARY
LIPSTICK BASE

| INGREDIENTS | PARTS BY WEIGHT | INCI NAME |
|---|---|---|
| Castor Oil | 24.61 | Castor Oil |
| POLYDERM PPI-CO[1] | 10.0 | N/A |
| DERMOL M-5[1] | 14.0 | Caprylic/Capric Triglycerides |
| Petralatum | 12.0 | Petralatum |
| POLYDERM PPI-D | 2.0 | N/A |
| Mineral Oil | 12.0 | Mineral Oil |
| Lanolin | 2.5 | Lanolin |
| DERMOLAN GLH[1] | 2.5 | Glycereth-7-Hydrox stearate |
| DERMOL 185[1] | 3.0 | Isostearyl Neopentanoate |
| DERMOL DID[1] | 2.0 | Diisopropyl Dilinoleate |

FORMULARY LIPSTICK BASE

| INGREDIENTS | PARTS BY WEIGHT | INCI NAME |
| --- | --- | --- |
| DERMACET AC[1] | 4.0 | Acetylated Cetyl Alcohols & Acetylated Lanolin " |
| Ozokerite | 2.5 | Ozokerite |
| DERMOL IPL[1] | 0.5 | Isopropyl Linoleate |
| Propyl Paraben | 0.06 | Propyl Paraben |
| Aloe Vera | 0.06 | Aloe Vera |
| BHA | 0.06 | Butylated Hydroxyanisole |
| Vitamin E | 0.06 | Alpha Tocopherol Acetate |
| PABA | 0.02 | p-Amino Benzoic Aci |
| Candelilla Wax | 16.00 | Candelilla Wax |

PROCEDURE:

To be ground and blended in the usual manner.

[1]ALZO INC.

FORMULARY POLYMERIC LIP GLOSS

| INGREDIENTS | %, WEIGHT | INCI NAME |
| --- | --- | --- |
| A. WAXENOL 801[1] | 2.0 | Arachidyl Propionate |
| Lanolin, USP Anhydrous | 4.0 | Lanolin |
| DERMOLAN GLH[1] | 4.0 | Glycereth-7-Hydroxystearate |
| Petralatum | 5.0 | Petralatum |
| DERMOL 25L | 10.0 | $C_{12}C_{15}$ Alcohols Lactate |
| Ozokerite #4 | 7.5 | Ozokerite |
| Castor Oil | 16.0 | Castor Oil |
| POLYDERM PPI-CO[1] | 8.2 | N/A |
| Beeswax | 7.5 | Beeswax |
| Carnauba Wax | 5.0 | Carnauba Wax |
| Methyl Paraben | 0.1 | Methyl Paraben |
| Tenox 11 | 0.1 | Butylated Hydroxy Anisol |
| B. Pigments | 1.6 | — |
| DERMOL IDO[1] | 15.0 | Isodecyl Oleate |
| Lunapearl BZ-CO-70 | 14.0 | — |

PROCEDURE:

1. Grind the color pigments in a portion of the DERMOL IDO; add the pearl and balance of the IDO to complete B. Melt A wax and oils to 80° C. Heat B to 70° C. and add to A.
2. Pour into molds at 75–80° C.

[1]ALZO INC.

FORMULARY POLYMERIC CONDITIONING SHAMPOO (PEARLESCENT)

| INGREDIENTS | %, WEIGHT | INCI NAME |
| --- | --- | --- |
| Water (Deionized) | 46.8 | |
| Dowicil-200[1] | 0.2 | Quaternium-15 |
| Foamquat SOAS[2] | 1.5 | Soyamidopropyl Ethyl-dimonium Ethosulfate |
| Polyderm PPI-CO[2] | 1.0 | N/A |
| Dermowax EGMS[2] | 0.5 | Glycol Stearate |
| Foamtaine CAB-G[2] (45%) | 20.0 | Cocamidopropyl Betaine |
| Bio-Terge AS[3] (40%) | 10.0 | Sodium Alpha Olefin Sulfonate |
| Stepanol WA Paste[3] (30%) | 20.0 | Sodium Lauryl Sulfate |
| Color | q.s. | |
| Fragrance | q.s. | |
| | 100.0 | |

FORMULARY POLYMERIC CONDITIONING SHAMPOO (PEARLESCENT)

| INGREDIENTS | %, WEIGHT | INCI NAME |
| --- | --- | --- |

PROCEDURE:

1. Heat water to 55–60° C. With fast stirring, slowly add Dowicil-200 and Foamquat SOAS. Mix to dissolve.
2. Add Polyderm PPI-CO and EGMS. Mix to dissolve.
3. With fast mixing, slowly add Foamtaine CAB-G, Alpha Olefin and Sodium Lauryl Sulfate.
5. When uniform, cool; add Color and Fragrance.

TYPICAL SPECIFICATIONS:

| Activity, %: | 22 |
| --- | --- |
| Viscosity: | 3,000 (Without Fragrance) |
| pH @ 25° C. | 7.0 |

[1]DOW CHEMICAL
[2]ALZO INC.
[3]STEPAN

What is claimed is:

1. A skin and personal care composition comprising 1% to 10% by weight of the reaction product of

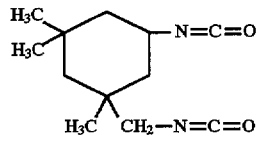

and

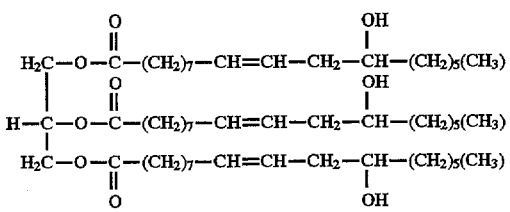

and also containing by weight:

4.0% PPG-30 Cetyl Ether 3.0% Diisopropyl Sebacate;

5.0% Isostearyl Neopentanoate Isocetyl Stearate;

4.0% Stearic acid;

6.0% Propylene Glycol Stearate;

1.0% Cetyl alcohol;

57.7% to 67.7% Deionized Water;

0.2% Quaternium-15;

1.0% Triethanolamine;

5.0% Acetamide MEA;

0.1% Fragrance.

2. A compound for use in personal care and cosmetic compositions, said compound comprising the reaction product of

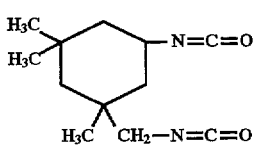

-continued
and

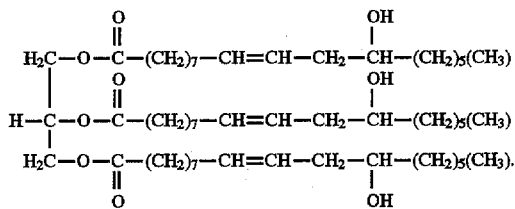

3. A compound for use in personal care and cosmetic compositions comprising the reaction product of isophorone diisocyanate and purified castor oil.

4. The compound according to claim 3 wherein said isophorone diisocyanate and said purified castor oil are reacted in a molar ratio of 1:2.

5. The skin and personal composition of claim 1 wherein the said composition is a polymeric moisturizing cream formulation containing by weight:
4.0% PPG-30 Cetyl Ether;
3.0% Diisopropyl Sebacate;
5.0% Isostearyl Neopentanoate Isocetyl Stearate;
4.0% Stearic Acid;
6.0% Propylene Glycol Stearate;
1.0% Cetyl Alcohol;
67.7% Deionized Water;
0.2% Quaternium-15;
1.0% Triethanolamine;
5.0% Acetamide MEA;
0.1% fragrance; and
3.0% of said compound of claim 1.

6. A skin and personal care composition wherein the said composition is a lip cream containing by weight:
12.0% Glycereth Monostearyl Erucate;
10.0% Tridecylneopentanoate;
15.0% Mineral Oil;
2.0% Cetearyl Alcohol (and) Ceteareth-20;
3.0% Cetyl Alcohol;
48% Deionized Water;
3.0% Linoleylamidopropylethonium Ethosulfate;
5.0% Propylene Glycol;
1.0% Propylene Glycol (and) Diazolidinyl Urea (and) Methylparaben (and) Propylparaben; and
1.0% of said compound of claim 2.

7. A skin and personal care composition wherein the said composition is a dry skin cream, formulation containing by weight:
4.0% Stearic Acid;
6.0% Tridecylneopentanoate;
2.0% Bis (Octyldodecyl Stearoyl) Dimer Dilinoleate;
0.5% Lanolin Oil
2.0% P E G- 40 Stearate
5.0% Mineral Oil
1.0% Dimethiconecopolyol;
3.0% Glycereth monstearyl erucate;
0.1% Tocopheryl Acetate;
55.0% Deionized Water;
3.0% Propylene Glycol;
0.2% Allantoin;
0.9% Triethanolamine, 99%;
15.0% Carbomer 934;
1.0% Propylene Glycol (and) Diazolidinyl Urea (and) Methylparaben (and) Propylparaben;
0.3% Fragrance; and,
1.0% of said compound of claim 2.

8. A skin and personal care composition wherein the said composition is a lipstick base containing by weight:
24.61% Castor Oil;
14.0% Caprylic/Capric Triglycerides;
12.0% Petrolatum;
2.0% 9,12-Octadecadienol Dimer Polymer with 3-isocyanatoethyl-3,5,5- Trimethylcyclohexyl Isocyanate;
12.0% Mineral Oil;
2.5% Lanolin;
2.5% Glycereth- 7 - hydroxy stearate;
3.0% Isostearyl Neopentanoate;
2.0% Diisopropyl Dilinoleate;
4.0% Acetylated Cetyl Alcohols and Acetylated Lanolin;
2.5% Ozokerite;
0.5% Isopropyl Linoleate;
0.06% Propyl Paraben;
0.06% Aloe Vera;
0.06% Butylated Hydroxyanisole;
0.06% Alpha Tocopherol Acetate;
0.02% p- Amino Benzoic Acid;
16.0% Candelilla Wax; and,
10.0% of said compound of claim 2.

9. A skin and personal care composition wherein said composition is a polymeric lip gloss formulation containing by weight:
2.0% Arachidyl Propionate;
4.0% Lanolin;
4.0% Glycereth-7-hydroxystearate;
5.0% Petrolatum;
10.0% C 12 C 15 Alcohols Lactate;
7.5% Ozokerite;
16.0% Castor Oil;
7.5% Beeswax
5.0% Carnauba Wax;
0.1% Methyl Paraben;
0.1% Butylated Hydroxy Anisol;
1.6% Pigments;
15.0% Isodecyl Oleate;
14.0% Lunapearl; and 8.2% of said compound of claim 2.

10. A skin and personal care composition wherein said composition is a polymeric conditioning shampoo containing by weight:
46.01% Deionized Water;
0.2% Quaternuim - 15;
1.5% Soyamidopropyl Ethyldimonium Ethosulfate;
0.5% Glycol Stearate;
20.0% Cocamidopropyl Betaine;
10.0% Sodium Alpha Olefin Sulfonate;
20.0% Sodium Lauryl Sulfate;
0.1% Color;
0.01% Fragrance; and,
1.0% of said compound of claim 2.

* * * * *